US 6,527,432 B2

(12) United States Patent
Kellogg et al.

(10) Patent No.: US 6,527,432 B2
(45) Date of Patent: Mar. 4, 2003

(54) BIDIRECTIONAL FLOW CENTRIFUGAL MICROFLUIDIC DEVICES

(75) Inventors: Gregory J. Kellogg, Cambridge, MA (US); Bruce L. Carvalho, Watertown, MA (US)

(73) Assignee: Tecan Trading AG, Baar (CH)

( * ) Notice: Subject to any disclaimer, the term of this patent is extended or adjusted under 35 U.S.C. 154(b) by 0 days.

(21) Appl. No.: 09/858,581

(22) Filed: May 15, 2001

(65) Prior Publication Data

US 2002/0097632 A1 Jul. 25, 2002

Related U.S. Application Data

(60) Provisional application No. 60/204,264, filed on May 15, 2000.

(51) Int. Cl.[7] .............................. B01F 1/00; B01L 3/02
(52) U.S. Cl. .................. 366/182.1; 366/220; 366/341; 366/349; 422/72; 422/64; 422/100
(58) Field of Search .................. 366/220, 341, 366/349, 182.1; 422/72, 64, 67, 103, 258, 100; 436/45

(56) References Cited

U.S. PATENT DOCUMENTS

| 3,679,367 A | * | 7/1972 | Negersmith et al. ......... 422/72 |
| 3,744,975 A |   | 7/1973 | Mailen |
| 4,030,834 A | * | 6/1977 | Bauer et al. ................... 422/72 |
| 4,154,793 A | * | 5/1979 | Guigan ........................ 422/72 |
| 4,894,204 A | * | 1/1990 | Cornut ........................ 422/72 |
| 5,061,381 A | * | 10/1991 | Burd .......................... 422/72 |
| 5,122,284 A | * | 6/1992 | Braynin et al. ............... 422/72 |
| 5,160,702 A |   | 11/1992 | Kopf-Sill et al. |
| 5,173,193 A | * | 12/1992 | Schembri ..................... 422/72 |
| 5,173,262 A | * | 12/1992 | Burtis et al. .................. 422/72 |
| 5,186,844 A | * | 2/1993 | Burd et al. ................... 422/72 |
| 5,242,606 A | * | 9/1993 | Braynin et al. ............... 422/72 |
| 5,242,803 A | * | 9/1993 | Burtis et al. .................. 422/72 |
| 5,300,779 A |   | 4/1994 | Hillman et al. |
| 5,304,348 A | * | 4/1994 | Burd et al. ................... 422/72 |
| 5,409,665 A | * | 4/1995 | Burd .......................... 422/72 |
| 5,457,053 A | * | 10/1995 | Burd et al. ................... 422/72 |
| 5,472,603 A | * | 12/1995 | Schembri ..................... 422/72 |
| 5,478,750 A | * | 12/1995 | Bernstein et al. ............. 422/64 |
| 5,496,520 A | * | 3/1996 | Kelton et al. ................. 422/72 |
| 5,518,930 A | * | 5/1996 | Burd .......................... 422/72 |
| 5,591,643 A | * | 1/1997 | Schembri ..................... 436/45 |
| 5,639,428 A | * | 6/1997 | Cottingham ................. 422/112 |
| 5,693,233 A | * | 12/1997 | Schembri ..................... 422/72 |
| 5,976,896 A | * | 11/1999 | Kumar et al. ................ 436/527 |
| 6,063,589 A | * | 5/2000 | Kellogg et al. ............... 435/24 |
| 6,143,248 A | * | 11/2000 | Kellogg et al. ............... 422/72 |
| 6,302,134 B1 | * | 10/2001 | Kellogg et al. ............... 137/74 |
| 6,361,958 B1 | * | 3/2002 | Shieh et al. ................... 435/7.1 |
| 6,399,361 B2 | * | 6/2002 | Brotherston et al. ...... 435/283.1 |

FOREIGN PATENT DOCUMENTS

| GB | 2341924 A | | 3/2000 |
| WO | WO 98/07019 | * | 2/1998 |

* cited by examiner

*Primary Examiner*—Tony G. Soohoo
(74) *Attorney, Agent, or Firm*—McDonnell Boehnen Hulbert & Berghoff

(57) ABSTRACT

This invention relates to methods and apparatus for performing microanalytic and microsynthetic analyses and procedures. The invention particularly provides microsystem platforms for achieving efficient mixing of one or a plurality of fluids on the surface of the platform when fluid flow is motivated by centripetal force produce by rotation.

27 Claims, 4 Drawing Sheets

FIG. 4A
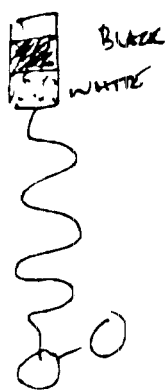
FIG. 4B
FIG. 4C
FIG. 4D
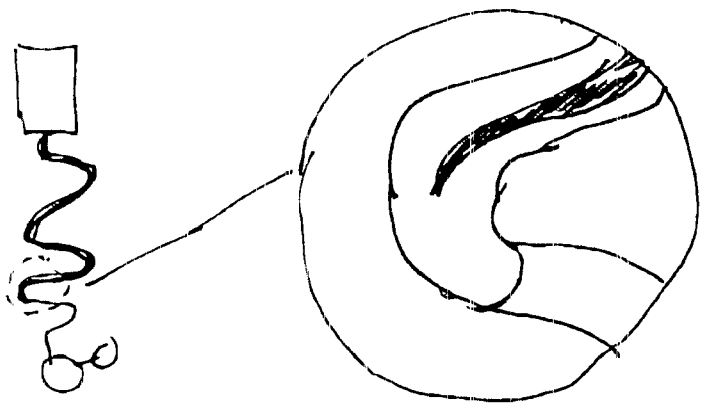
FIG. 4E
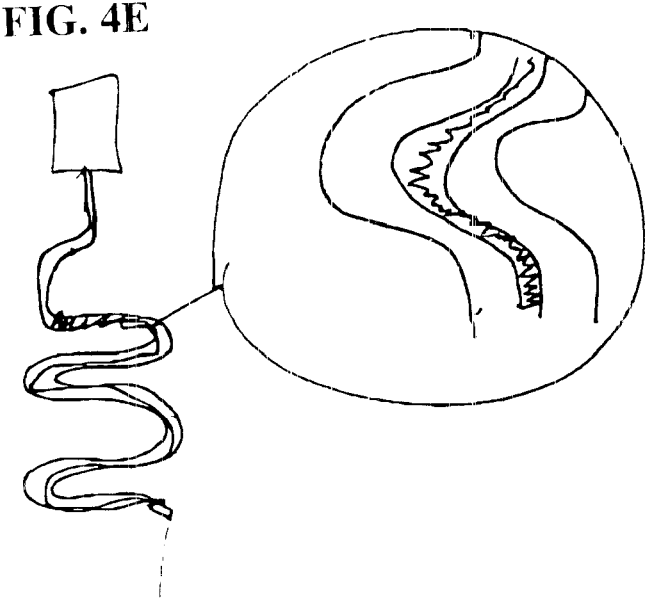
FIG. 4F

BIDIRECTIONAL FLOW CENTRIFUGAL MICROFLUIDIC DEVICES

This application claims priority to U.S. Provisional Application, Serial No. 60/204,264, filed May 15, 2000, the disclosure of which is explicitly incorporated by reference herein.

BACKGROUND OF THE INVENTION

1. Field of the Invention

This invention relates to chemical and biological assay technology carried out in disposable plastic assemblies, and in particular the devices referred to as microfluidic systems as disclosed in U.S. Pat. No. 6,063,589, issued May 16, 2000, and co-owned and co-pending patent applications U.S. Ser. No. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; and Ser. No. 09/315,114, filed May 19, 1999, the disclosures of each of which are explicitly incorporated by reference herein.

2. Background of the Related Art

Microfluidic systems are closed interconnected networks/systems of channels and reservoirs with characteristic dimensions ranging from microns to millimeters. By introducing fluids, reagents and samples into the devices, chemical and biological assays can be carried out in an integrated and automated way. In a conventional assay, two or more fluids are mixed and incubated within a microfluidic device and during, or after, this incubation period, a reaction product may be detected. It is typically the case that this microfluidic device, specifically the depths, cross-sectional dimensions and connectivity and layout of the microfluidic systems, defines the relative volumes of these fluids.

A problem in the art is that microfluidic devices, once fabricated, do not allow the user to redefine the relative volumes of the fluids to be mixed. An additional problem in the art concerns the degree and efficiency of mixing. Because the flow within a microfluidic device is laminar, mixing is brought about through mass diffusion. A typical mixing device consists of a long capillary. Two or more fluids may enter this capillary as separate fluids and leave as a single fluid. The degree of mixing can be enhanced and the time to mix these fluids can be decreased by decreasing the cross-sectional dimension of the capillary and by increasing the length of the capillary channel, but such a device can occupy a fair amount of space within a microfluidic system.

SUMMARY OF THE INVENTION

This invention describes the use of air-ballasts and microchannels with graded surface properties to allow for bidirectional fluid flow. Bidirectional flow within microchannels allows different fluids to laminate and mix within a microchannel. The combination of air-ballasts, microchannels with graded surface properties, (passive) capillary valves and (active) wax valves allow for mixing and aliquotting of arbitrary volumes within a defined microfluidic system.

DESCRIPTION OF THE FIGURES

FIG. 4 describes mixing in a microchannel.

DETAILED DESCRIPTION OF THE PREFERRED EMBODIMENTS

Figure 1:
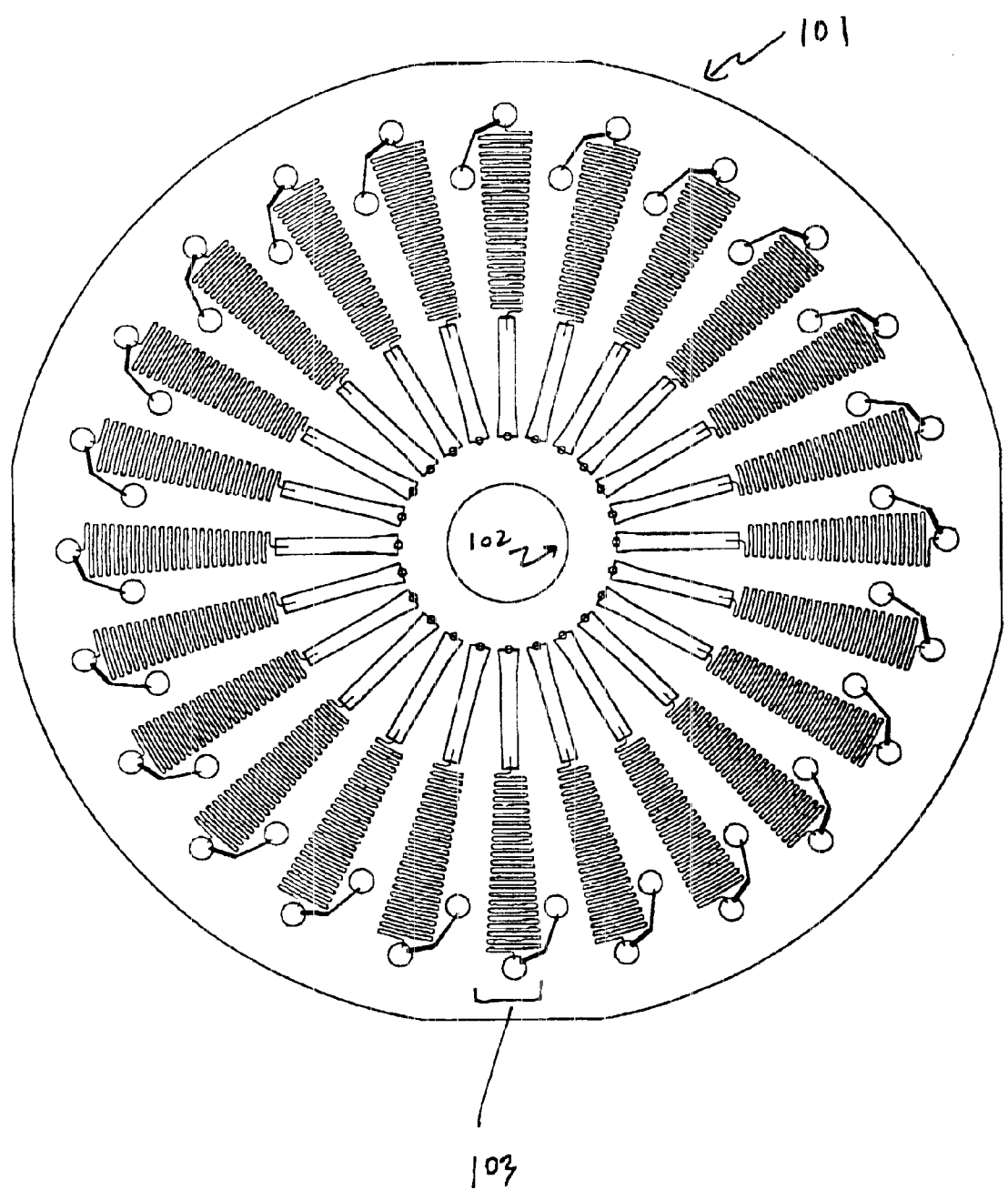
FIG. 1 describes bidirectional flow centrifugal microfluidic devices, azimuthally arrayed on a disc.

This invention provides a microplatform and a micromanipulation device as disclosed in co-owned U.S. Pat. No. 6,063,589, issued May 16, 2000, and co-owned and co-pending patent applications U.S. Ser. No. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, the disclosures of each of which are explicitly incorporated by reference herein, adapted for performing efficient mixing of a plurality of different fluids and solutions.

For the purposes of this invention, the term "sample" will be understood to encompass any fluid, solution or mixture, either isolated or detected as a constituent of a more complex mixture, or synthesized from precursor species.

For the purposes of this invention, the term "a centripetally motivated fluid micromanipulation apparatus" is intended to include analytical centrifuges and rotors, microscale centrifugal separation apparatuses, and most particularly the microsystems platforms and disk handling apparatuses as described in co-owned U.S. Pat. No. 6,063,589, issued May 16, 2000, and co-owned and co-pending patent applications U.S. Ser. No. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, the disclosures of each of which are explicitly incorporated by reference herein.

For the purposes of this invention, the term "Microsystems platform" is intended to include centripetally-motivated microfluidics arrays as described in co-owned U.S. Pat. No. 6,063,589, issued May 16, 2000, and co-owned and co-pending patent applications U.S. Ser. No. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, the disclosures of each of which are explicitly incorporated by reference herein.

For the purposes of this invention, the terms "capillary", "microcapillary" and "microchannel" will be understood to be interchangeable and to be constructed of either wetting or non-wetting materials where appropriate.

For the purposes of this invention, the term "capillary junction" will be understood to mean a region in a capillary or other flow path where surface or capillary forces are exploited to retard or promote fluid flow. A capillary junction is provided as a pocket, depression or chamber in a hydrophilic substrate that has a greater depth (vertically within the platform layer) and/or a greater width (horizontally within the platform layer) that the fluidics component (such as a microchannel) to which it is fluidly connected. For liquids having a contact angle less than 90° (such as aqueous solutions on platforms made with most plastics, glass and silica), flow is impeded as the channel cross-section increases at the interface of the capillary junction. The force hindering flow is produced by capillary pressure, that is inversely proportional to the cross sectional dimensions of the channel and directly proportional to the surface tension of the liquid, multiplied by the cosine of the contact angle of the fluid in contact with the material comprising the channel. The factors relating to capillarity in microchannels according to this invention have been discussed in co-owned U.S. Pat. No. 6,063,589, issued May 12, 2000 and in co-owned and co-pending U.S. patent application, Ser. No. 08/910,726, filed Aug. 12, 1997, incorporated by reference in its entirety herein.

Capillary junctions can be constructed in at least three ways. In one embodiment, a capillary junction is formed at the junction of two components wherein one or both of the lateral dimensions of one component is larger than the lateral dimension(s) of the other component. As an example, in microfluidics components made from "wetting" or "wettable" materials, such a junction occurs at an enlargement of a capillary as described in co-owned and co-pending U.S. Serial Nos. U.S. Ser. No. 08/761,063, filed Dec. 5, 1996; Ser. No. 08/768,990, filed Dec. 18, 1996; and Ser. No. 08/910, 726, filed Aug. 12, 1997. Fluid flow through capillaries is inhibited at such junctions. At junctions of components made from non-wetting or non-wettable materials, on the other hand, a constriction in the fluid path, such as the exit from a chamber or reservoir into a capillary, produces a capillary junction that inhibits flow. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

A second embodiment of a capillary junction is formed using a component having differential surface treatment of a capillary or flow-path. For example, a channel that is hydrophilic (that is, wettable) may be treated to have discrete regions of hydrophobicity (that is, non-wettable). A fluid flowing through such a channel will do so through the hydrophilic areas, while flow will be impeded as the fluid-vapor meniscus impinges upon the hydrophobic zone.

The third embodiment of a capillary junction according to the invention is provided for components having changes in both lateral dimension and surface properties. An example of such a junction is a microchannel opening into a hydrophobic component (microchannel or reservoir) having a larger lateral dimension. Those of ordinary skill will appreciate how capillary junctions according to the invention can be created at the juncture of components having different sizes in their lateral dimensions, different hydrophilic properties, or both.

For the purposes of this invention, the term "capillary action" will be understood to mean fluid flow in the absence of rotational motion or centripetal force applied to a fluid on a rotor or platform of the invention and is due to a partially or completely wettable surface.

For the purposes of this invention, the term "capillary microvalve" will be understood to mean a capillary microchannel comprising a capillary junction whereby fluid flow is impeded and can be motivated by the application of pressure on a fluid, typically by centripetal force created by rotation of the rotor or platform of the invention. Capillary microvalves will be understood to comprise capillary junctions that can be overcome by increasing the hydrodynamic pressure on the fluid at the junction, most preferably by increasing the rotational speed of the platform.

For the purposes of this invention, the term "in fluid communication" or "fluidly connected" is intended to define components that are operably interconnected to allow fluid flow between components.

For the purposes of this invention, the term "reservoir," "assay chamber," "fluid holding chamber," "collection chamber" and "detection chamber" will be understood to mean a defined volume on a microsystems platform of the invention comprising a fluid.

For the purposes of this invention, the terms "entry port" and "fluid input port" will be understood to mean an opening on a microsystems platform of the invention comprising a means for applying a fluid to the platform.

For the purposes of this invention, the term "air displacement channels" will be understood to include ports in the surface of the platform that are contiguous with the components (such as microchannels, chambers and reservoirs) on the platform, and that comprise vents and microchannels that permit displacement of air from components of the platforms and rotors by fluid movement.

The microplatforms of the invention (preferably and hereinafter collectively referred to as "disks"; for the purposes of this invention, the terms "microplatform", "microsystems platform" and "disk" are considered to be interchangeable) are provided to comprise one or a multiplicity of microsynthetic or microanalytic systems (termed "microfluidics structures" herein). Such microfluidics structures in turn comprise combinations of related components as described in further detail herein that are operably interconnected to allow fluid flow between components upon rotation of the disk. These components can be microfabricated as described below either integral to the disk or as modules attached to, placed upon, in contact with or embedded in the disk. For the purposes of this invention, the term "microfabricated" refers to processes that allow production of these structures on the sub-millimeter scale. These processes include but are not restricted to molding, photolithography, etching, stamping and other means that are familiar to those skilled in the art.

The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, the disclosures of each of which are explicitly incorporated by reference herein.

The invention provides a combination of specifically-adapted microplatforms that are rotatable, analytic/synthetic microvolume assay platforms, and a micromanipulation device for manipulating the platform to achieve fluid movement on the platform arising from centripetal force on the platform as result of rotation. The platform of the invention is preferably and advantageously a circular disk; however, any platform capable of being rotated to impart centripetal force for a fluid on the platform is intended to fall within the scope of the invention. The micromanipulation devices of the invention are more fully described in co-owned and co-pending U.S. Serial Nos. U.S. Ser. No. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; and Ser. No. 09/315,114, filed May 19, 1999, the disclosures of each of which are explicitly incorporated by reference herein.

The components of the platforms of the invention are in fluidic contract with one another. In preferred embodiments, fluidic contact is provided by microchannels comprising the surface of the platforms of the invention. Microchannel sizes are optimally determined by specific applications and by the amount of and delivery rates of fluids required for each particular embodiment of the platforms and methods of the invention. Microchannel sizes can range from 0.1 μm to a value close to the thickness of the disk (e.g., about 1 mm); in preferred embodiments, the interior dimension of the microchannel is from 0.5 μm to about 500 μm. Microchannel and reservoir shapes can be trapezoid, circular or other geometric shapes as required. Microchannels preferably are embedded in a microsystem platform having a thickness of about 0.1 to 25 mm, wherein the cross-sectional dimension of the microchannels across the thickness dimension of the platform is less than 1 mm, and can be from 1 to 90 percent of said cross-sectional dimension of the platform. Sample reservoirs, reagent reservoirs, reaction chambers, collection chambers, detections chambers and sample inlet and outlet ports preferably are embedded in a microsystem platform having a thickness of about 0.1 to 25 mm, wherein the cross-sectional dimension of the microchannels across the thickness dimension of the platform is from 1 to 75 percent of said cross-sectional dimension of the platform. In preferred embodiments, delivery of fluids through such channels is achieved by the coincident rotation of the platform for a time and at a rotational velocity sufficient to motivate fluid movement between the desired components.

Platforms of the invention such as disks and the microfluidics components comprising such platforms are advantageously provided having a variety of composition and surface coatings appropriate for particular applications. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces as described below. The platforms may also be made from thermoset materials such as polyurethane and poly(dimethyl siloxane) (PDMS). Also provided by the invention are platforms made of composites or combinations of these materials; for example, platforms manufactures of a plastic material having embedded therein an optically transparent glass surface comprising the detection chamber of the platform. Alternately, platforms composed of layers made from different materials may be made. The surface properties of these materials may be modified for specific applications, as disclosed in co-owned U.S. Pat. No. 6,063,589, issued May 16, 2000, and co-owned and co-pending patent applications U.S. Ser. No. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; and Ser. No. 09/315,114, filed May 19, 1999, the disclosures of each of which are explicitly incorporated by reference herein.

Preferably, the disk incorporates microfabricated mechanical, optical, and fluidic control components on platforms made from, for example, plastic, silica, quartz, metal or ceramic. These structures are constructed on a sub-millimeter scale by molding, photolithography, etching, stamping or other appropriate means, as described in more detail below. It will also be recognized that platforms comprising a multiplicity of the microfluidic structures are also encompassed by the invention, wherein individual combinations of microfluidics and reservoirs, or such reservoirs shared in common, are provided fluidly connected thereto. An example of such a platform is shown in FIG. 1.

Platform Manufacture and Assembly

Referring now to the Figures for a more thorough description of the invention, FIG. 1 show a plan view of a disc of the microsystem platform. In this embodiment, platform 100 is composed of at least two layers, a fluidics layer 101 and a sealing layer 199 (not shown). At the center of this disc is a hole 102 for affixing the disc to a rotary spindle; other means such as extruded features for connection to a spindle, or features not on the axis of the disc, are also possible.

The construction of this disc is made to illustrate the concept of centrifugally driven, bidirectional flow. It is understood that the elements shown here may be complete for the purposes of performing certain assays or fluid processing, or may be part of a larger system of reservoirs and channels. This disc illustrates that identical assays may be made by repeating assay structures around the disc at a given radius. Here, structure 103 is repeated azimuthally around the platform layer 101.

Platform 100 is preferably provided in the shape of a disc, a circular planar platform having a diameter of from about 10 mm to about 50 mm and a thickness of from about 0.1 mm to about 25 mm. Each layer comprising the platform preferably has a diameter that is substantially the same as the other layers, although in some embodiments the diameters of the different layers are not required to completely match. Each layer has a thickness ranging from about 0.1 mm to about 25 mm, said thickness depending in part on the volumetric capacity of the microfluidics components contained therein. A variety of materials may be used to fabricate 101 but preferred materials are polymer materials, including thermoplastics, thermosets and elastomeric materials. Examples of thermoplastic materials include acrylics, polycarbonates, cyclic olefin copolymers and polyolefins such as polypropylene. Polyurethane thermosets and silicone are examples of thermoset and elastomeric materials, respectively. A variety of standard fabrication methods may be used to define features within 101, including high-speed machining, injection molding, compression injection molding and embossing. Reaction injection molding may be used to fabricate discs made with thermoset materials. The sealing layer (199) may consist of thermoplastic lids that are diffusion bonded to the 101 with temperature and pressure or adhesive films that are applied with hand pressure. Depending on the choice of materials of 101 and 199, it is possible to functionalize the opposing surfaces of 101 and 199 to achieve chemically bond 101 to 199, when the surfaces are brought into contact.

Figure 2:
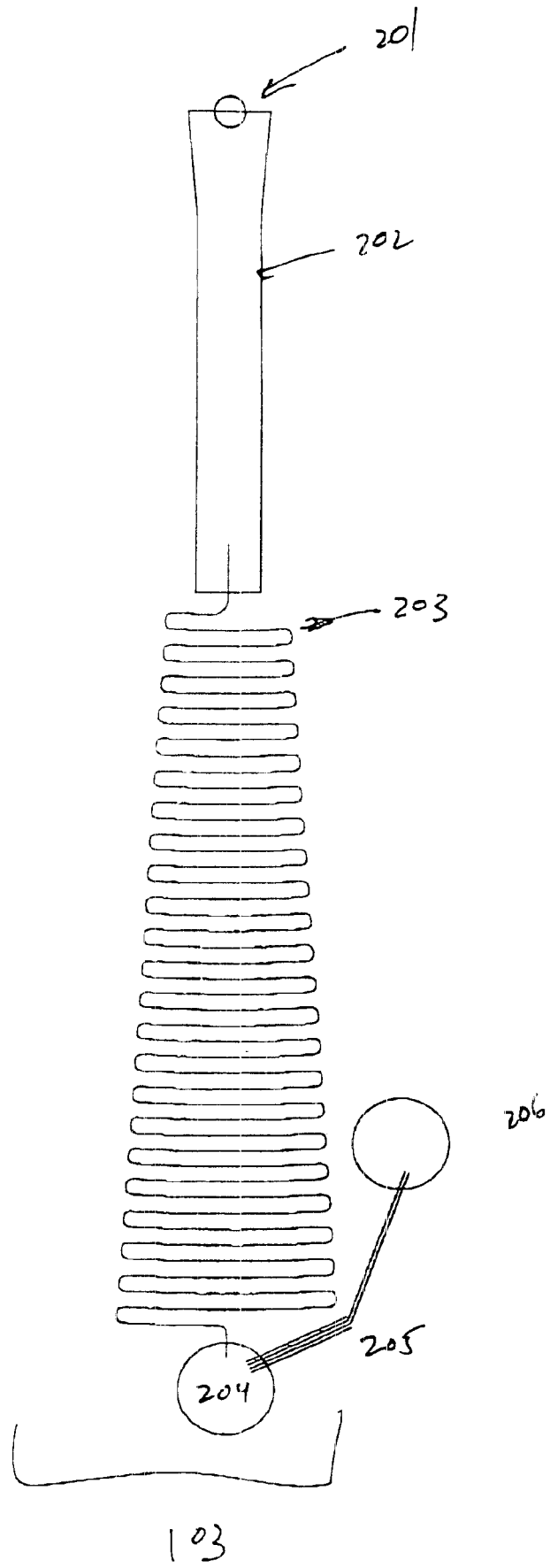
FIG. 2 describes an individual bidirectional flow device.

Referring to FIG. 2, a single structure for the performance of a mixing assay is illustrated. Among the components of the structure are a fluid entry port 201 through which fluids may be added to the reservoir 202. Reservoir 202 is preferably sized to contain the maximum amount of fluid that might be processed in a series of assays, being in the range of 1 nL to 100 μL. Extending from reservoir 202 is microchannel 203. Microchannel 203 is preferably sized such that its volume is between 1 and 2 times the maximum volume of reservoir 202 and with a cross-sectional size in the range of 5–500 μm. At the radially-distal end of 203 is a detection cuvette 204 with a volume between 0.5 and 2 times the maximum volume of the reservoir 202. Connected to 204 by channel 205 is an air-ballast 206, an enclosed reservoir containing air or another gas. The size chosen for 206 is a function of the desired operating parameters of the device and is generally in the range of 0.1–10 times the maximum volume of the reservoir 202.

Figure 3A:
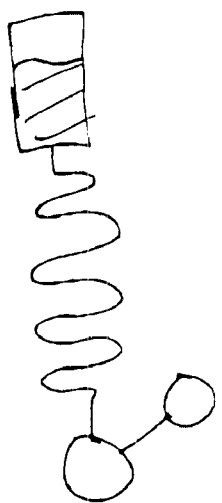
FIG. 3 describes a sequence of flow events at different disc rotation rates.
Figure 3B:
Figure 3C:
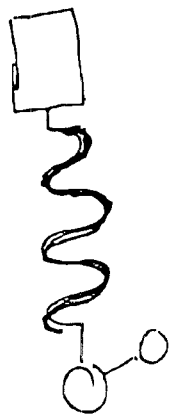
Figure 3D:

In use, the disc would function in the following fashion. A first liquid sample is added via port 201 to reservoir 202. The device may be rotated to drive the fluid to the radially-distal end of the reservoir. A second fluid is added to port 201. The situation at rest is illustrated in FIG. 3a. The disc is now spun at a rotational speed sufficient to drive the fluids into channel 203. Opposing flow into 203 is a restoring force due to the compression of the trapped air in the remainder of 203, the cuvette 204, channel 205, and ballast 206. For any mode of mixing, the fluid must be driven such that the entire combined volume has entered the channel; however, the rotational rate must not be so high as to result in the fluid leaving channel 203 and entering reservoir 204.

The rotational rates necessary may be determined from the following considerations. It can be shown that the hydrostatic pressure generated by a column, reservoir, or channel of liquid due to rotation is $$P_R = \rho \omega^2 \Delta r \bar{r} \quad (1)$$

where $\rho$ is the density of the fluid (average density in the case of multiple fluids); $\omega$ is the angular velocity with which the device rotates; $\Delta r$ is the radial extent of the liquid, that is, the difference in radial position between the liquid interface in contact with the compressed air and the radial position of the trailing interface of the liquid with the air in 202; and $<r>$ is the average radial position of the liquid as defined by the radial position of those two interfaces.

Let the various volumes be defined as follows: $V_T$=total combined fluid volumes added; $V_C$=volume of channel 203; $V_B$=volume of 204 plus that of 205 and 206. As the liquid enters 203, it displaces some of the volume of 203; if the device is rotated with sufficient speed, all fluid leaves 202, and the displaced volume can be greater than $V_T$. Let the volume of 203 that is displaced volume for a specific radial position of the liquid of interest be defined as $V_D$. If the fluid has not entered chamber 204, the restoring pressure due to compressed gas is then $$P_C = P_{ATM} \frac{V_D}{V_c + V_B} \quad (2)$$

Where $P_{ATM}$ is the ambient pressure when the fluid is loaded into the device. Fluid motion will halt when $$\rho \omega^2 \Delta r \bar{r} = P_{ATM} \frac{V_D}{V_c + V_B} \quad (3)$$

$$\omega = \left[\frac{P_{ATM}}{\rho \Delta r \bar{r}} \left(\frac{V_D}{V_c + V_B}\right)\right]^{1/2}$$

This relationship allows one to determine the appropriate rotational velocity for desired displacement volume.

FIG. 3 illustrates the motion of the fluid. In FIG. 3a, the first and second fluids are seen to be layered, due to being added sequentially. In FIG. 3b, the fluids are shown as they begin to move into 203 at a non-zero rotational rate. In FIG. 3c, has completely entered 203 and is stationary at a rotational rate given in Eq. 3. As the rotational rate is decreased, as in FIG. 3d, the fluid is expelled from the channel 203, until it is completely expelled into 202 at zero rotational rate.

The device illustrated in the figures is only one possible construction for affecting bidirectional flow. Alternative constructions include a reservoir 202 that is also a detection cuvette. For such a device, a single ballast chamber may be at the end of channel 203, with no additional detection cuvette.

Another alternative embodiment uses surface forces, rather than forces due to compression of gas, to drive flow in the reverse direction. If, for example, the surfaces of the disc are coated or functionalized to have a contact angle of greater than 90 degrees, surface energy considerations show that the preferred state of fluids is one with minimum contact with the hydrophobic surfaces. Aqueous liquids in hydrophobic channels are naturally expelled into chambers with smaller surface area to volume ratios. It should be noted that fluid in a channel with constant cross-section is subjected to no force driving in either direction along the channel. Only if the cross-section decreases along the outward direction will a restoring force exist. In such an application, either gradual or abrupt narrowing of channels can provide this force.

Another alternative embodiment can use surfaces with a gradient in contact angle along the flow path in the channel. A channel of fixed cross-section will provide a restoring force if the contact angle at the leading edge of the fluid is larger than that at the trailing edge of the liquid, that is, the surface grows progressively more hydrophobic along the flow path. Such a device may be fabricated through surface functionalization and patterning of hydrophobic patches on the surface of a channel with fixed cross-section.

Combinations of surface treatment and trapped air may also be used. For example, the all surfaces in the disc of FIGS. 1–3 may be treated to be hydrophobic. This has the advantage of preventing condensation of liquid onto surfaces if the liquid is heated. Heated liquids preferentially recondense onto the air-liquid interface rather than onto hydrophobic surfaces in such cases.

The use of the device for mixing is now demonstrated. In FIG. 4a, the first and second fluids are seen to be layered, due to being added sequentially. In FIG. 4b, the fluids are shown as they begin to move into 203 at a non-zero rotational rate. In FIG. 4c, has completely entered 203 and is stationary at a rotational rate given in Eq. 3. FIG. 4d is a magnified view of the fluid in the channel. It is not to scale, and the lateral dimension is exaggerated for clarity. The shape of the interface between the two fluids is seen to be a broadening along the direction of the channel. This is due to the laminar flow that occurs in small channels for low flow velocities and is a familiar feature from flow injection analysis. Note also that this is a cross-sectional representation, and that the broadening exists three-dimensionally and is a function of the inverse second power of the lateral channel dimensions. The important feature in FIG. 4d is that there is a large amount of interface between fluids A and B relative to the interface seen in FIG. 4a, and that the average distance of elements of fluid A from elements of fluid B is much smaller than in FIG. 4a.

More interface may be created between the fluids by driving them further into 203 by approximately ½ of the length occupied in FIG. 4b. FIG. 4e shows this situation. Here the interface between the two fluids occupies most of the length of the fluid column within 203.

Diffusion now acts to mix the fluids. Diffusional timescales are of the order of $$t \approx \frac{x^2}{D} \quad (4)$$

where x is distance over which diffusion must take place and D is the diffusion constant of chemical species, molecules, etc., which must be mixed. For example, if $x=100 \mu m$ and $D=5 \times 10^{-6}$ cm$^2$s$^{-1}$, t=20 seconds. In this case, the relevant dimension is the lateral size of the channel.

In order to ensure complete mixing, the device is brought to near 0 rotational speed, and the fluid is expelled by air pressure into 202, as shown in FIG. 4f. The device is then accelerated once again to drive fluids into 203 the appropriate distance. Multiple iterations of acceleration, holding, and deceleration allow additional fluid motion within reservoir 202 to provide additional mixing.

Additional fluids may be added via 201 and the mixing process repeated.

The device is then rotated at a second, higher rotational velocity, at which point it is expelled into cuvette 204. Air from channel 205 and ballast 206 then enters the end of 203; a pathway for air from 205 into 203 relieves the restoring force on the fluid already present in 204, and the device may be slowed while fluid is retained in 204.

The theoretical effectiveness of the mixing device may be compared to the diffusional mixing which would occur in reservoir 202 without the use of bidirectional motion. Assume 202 is a cube designed to contain 8 $\mu$L and as such is 2 mm×2 mm×2 mm in size. If two fluids are added sequentially with volumes of 4 $\mu$L and allowed to diffusionally mix, the expected time for this mixing is over 2 hours. This is in contrast to perhaps 2 minutes to effect 5 acceleration/hold/deceleration cycles using a 100 $\mu$m channel. Even volumes of 100 nL may require up to 10 minutes to diffusionally mix without the use of bidirectional flow.

It can be seen that the device as illustrated is capable of performing homogeneous assays in which active mixing must take place. The turnover of p-nitrophenol phosphate by alkaline phosphatase in the presence of theophylline is a model system for examining enzyme inhibition and requires efficient mixing of the enzyme and inhibitor before the addition of substrate. This enzymatic reaction can be monitored calorimetrically through the conversion of p-nitrophenol phosphate to p-nitrophenol, which is yellow and absorbs at wavelength of 410 nm. The absorbance at, or near, 410 nm decreases as the inhibitor (theophylline) concentration is increased. To perform such an assay in a bidirectional flow centrifugal microfluidic device, an aliquot of enzyme solution would be pipetted into the device, the disc would be rotated at a rotation rate sufficient to drive the fluid into the reservoir (202) and away from the entry port (201), an aliquot of inhibitor solution would then be pipetted into the device and the disc would undergo an acceleration/hold/deceleration cycle to allow for dispersional and diffusional mixing of the enzyme and inhibitor solutions within the channel (203) and reservoir (202), The calculation above shows that hold times of approximately 20 seconds are required to allow for diffusional mixing across 100 $\mu$m (assuming a diffusion coefficient of $5 \times 10^{-6}$ cm$^2$s$^{-1}$). After several acceleration/hold/deceleration cycles, disc rotation would be stopped and an aliquot of substrate solution would be pipetted into the device. A similar sequence of acceleration/hold/deceleration cycles would be performed to allow for mixing of enzyme/inhibitor with substrate.

Bidirectional flow can also be used to perform polymerase chain reaction (PCR) on a disc. In this application, the disc of FIG. 1 forms a mechanical and thermal contact with a co-rotatable platen. Electrical signals are distributed from a stationary power and control unit to the rotating platen through the use of an electrical commutator. In a simplified version of this idea, the surface of the platen has three bands of annular resistive heaters, each maintained at temperatures appropriate for the denaturation, annealing and extension of nucleic acids in the PCR process. More specifically, the heaters are arranged on the platen so that meandering capillary (203) has three distinct temperature when the disc is mated to the platen. Bidirectional flow can be used to drive fluid across these three different temperature zones. And because the ratio of surface to volume can be quite high within a microchannel, it is expected that fluid that traverses a defined temperature zone quickly comes to the temperature of this zone, thereby allowing the reaction to take place. A recent report by Chiou et al. demonstrates the use of gas to drive plugs of fluid through capillaries that are in thermal contact with a set of heaters; when used to perform PCR, it was found that a 500 base pair product could be amplified in 23 minutes with 30 complete temperature cycles and 78% amplification efficiency (J. Chiou, P. Matsudaira, A. Sonin and D. Erlich, "A Closed-Cycle Capillary Polymerase Chain Reaction Machine, Analytical Chemistry, 2001, 73, 2018–2021).

Bidirectional flow may also be used to perform inhomogeneous assays in the following fashion. Referring to FIG. 4, the device may be manufactured such that immunochemicals or other ligands are immobilized into the channel 203, for either the entire length of the channel or for a portion. A fluid sample is added to 202. The sample is driven into channel 203 cyclically as described above, allowing molecules within the fluid to bind to the ligands on the surface of the channel. The disc is then rotated at its third rotational rate, sufficient to drive all fluid into chamber 204; the emptying of 203 removes the restoring force. A second fluid may be added now, for example, a complementary molecule which may can bind to the molecule of interest whose presence is being assayed in the first fluid. This in turn may be bound to gold colloid particles for visual detection, or linked to enzymes for exposure to substrate. The liquid is now driven bidirectionally into the channel, and the complementary molecule allowed to bind to the first, immobilized molecule of the analyte. Direct visual detection in reflection mode using blue light will reveal the presence of gold colloid particles. For enzyme-linked complements, the process may be repeated with a third fluid consist of substrate for the enzyme; action of the enzyme may cause a colored or fluorescent product to be formed.

An important element of bidirectional flow in such an inhomogeneous assay is that the multiple passes of fluid across the surface covered with immobilized ligand allows trace amounts of analyte to be concentrated into a small area of the surface. It is possible to bind all of the anaylte in a large volume of liquid onto a small area much more quickly than could be achieved by bulk diffusion in an unmoving fluid.

Another application of such a method is nucleic acid hybridization. Complementary strands of DNA or RNA of interest may be immobilized into channels or intermediate reservoirs between 202 and 204. If necessary, the nucleic acids in the fluid sample may be denatured by application of heat, and then driven across the immobilized nucleic acids. Detection may be performed using common methods such as molecular beacons or intercalating dyes for double-stranded DNA.

This invention is additionally taught through the non-limiting example described below.

EXAMPLE 1

An experimental demonstration of bidirectional flow in a centrifugal microfluidic device was performed. Discs were fabricated from cast acrylic sheet (PMMA, ICI Acrylics, St.

Louis, Mo.) using a computer controlled milling machine (Benchman VMC-4000, Light Machines Corp., Manchester, N.H.) and a selection of end-mills that ranged in diameter from 250 µm to 1.6 mm. The machined acrylic surfaces were polished with methylene chloride vapor and then sealed with a layer of doubled-sided tape (467 MP Hi Performance Adhesive, 3M, Minneapolis, Minn.) and subsequently backed with a white polyester sheet. Liquids were pumped through the channels by rotating the discs on a spindle driven by a dc servomotor with an integral optical encoder (DC MicroMotor 3042/HEDS-55401, MicroMo, Clearwater, Fla.). The servomotor was operated via a motor controller card (PIC-Servo, HdB Electronics, Redwood City, Calif.) and a host PC using a program written in Visual Basic (Microscoft, Redmond, Wash.). The speed of the motor could be programmed to give rates of rotation between 0 and 4600 rpm. The encoder triggered external devices such as a tachometer, a stroboscope and frame buffer. Liquid flow was monitored using stroboscopic video microscopy. A fast response stroboscope (NovaStrobe DA116, Monarch Instruments, Amherst, N.H.) was triggered by the encoder and illuminated the spinning disc for 30 µs at each revolution. An image of the spinning disc was continually recorded by a ⅓ inch CCD color video camera (GP-KR222, Panasonic, Tokyo, Japan) with macrofocus zoom lens. The rate of rotation was recorded by the tachometer (08212, Cole-Parmer, Veron Hills, Ill.) and displayed simultaneously using a digital video mixer. To give a continuous illuminated image of the disc, dark frames were filtered out using a frame buffer (Ultra II, Coreco, Saint-Laurent, Quebec, Canada). The experiments described in this example were performed with food colored aqueous solutions.

As described in FIG. 2, a bidirectional flow centrifugal microfluidic device may consist of an entry port, an entry reservoir, a meandering capillary, a detection cuvette, and an air-ballast, all in fluid communication. As described in FIG. 1, bidirectional flow devices may be arrayed around the circumference of a circular disc and aligned so that fluid can flow back and forth between positions close to the inner and outer diameters of the disc. For this particular set of experiments, a bidirectional flow device was fabricated using the designs of FIGS. 1 and 2. The device was located on discs such that the center of the detection cuvette was at a distance of 54.4 mm from the center of rotation. The entry ports were sized to easily accommodate a plastic pipette tip and to allow air to escape as fluid was dispensed into the device. The entry reservoir (202) acommodated 15 µL with a length, width and depth of 15 mm, 2 mm and 0.5 mm, respectively. The meandering capillary (203) had a depth and cross-section of approximately 250 µm and had a volume of 15 µL so that all of the fluid could be driven from the entry reservoir into the channel at high rotation rates; the diameter and depth of the detection cuvette (204) were 3 mm and 0.5 mm, respectively, yielding a volume of approximately 3.5 µL; the volume of the air-ballast (206) was fixed close to 16 µL so that it would be possible to drive fluid from the meandering capillary to the detection cuvette. It was found that with a smaller air-ballast, the restoring forces were too high for the instrumentation at hand and fluid could not be driven into the detection cuvette at achievable rotation rates; significantly larger air-ballasts did not provide enough restoring force to rapidly drive the fluid from the meandering capillary back into the entry reservoir to achieve the required degree of mixing. It was experimentally determined that spinning this device with 12 µL of aqueous solution at 4600 rpm for 30 seconds was sufficient to fill the detection cuvette and that after stopping the disc rotation, an amount of fluid remained within the detection cuvette defined by the volume of the detection cuvette that is radially outboard of the junction between 205 and 204.

The table below reports the extent of the fluid front for a number of sequential rotation rates.

| Elapsed Time (seconds) | Rotation Rate (rpm) | Radial Position of Fluid Front |
|---|---|---|
| 0 | 500 | 30.0 mm |
| 20 | 1500 | 35.1 mm |
| 40 | 500 | 30.0 mm |
| 60 | 1500 | 35.1 mm |
| 80 | 500 | 30.0 mm |
| 100 | 1500 | 35.1 mm |
| 120 | 500 | 30.0 mm |
| 140 | 2300 | 41.7 mm |
| 160 | 500 | 29.5 mm |
| 180 | 2300 | 41.7 mm |
| 200 | 500 | 29.5 mm |
| 260 | 3800 | 50.9 mm |
| 290 | 4000 | 54.4 mm |
| 320 | 4200 | 54.4 mm |
| 350 | 4400 | 54.4 mm |
| 360 | 4600 | 54.4 mm |
| 390 | 0 | 54.4 mm |

It is worth noting that 4000 rpm fluid begins to flow into the detection cuvett (204) but it takes an increased rotation rate of 4600 rpm to fill the cuvette up to the junction of 205 and 204.

This example shows that bidirectional flow can be achieved in a microfluidic device with the combination of a centrifugal drive and air-ballasts.

It should be understood that the foregoing disclosure emphasizes certain specific embodiments of the invention and that all modifications or alternatives equivalent thereto are within the spirit and scope of the invention.

What is claimed is:

1. A centripetally-motivated microsystems platform comprising:
   a rotatable platform comprising a substrate having an axis of rotation and a surface comprising one or a multiplicity of microfluidics structures embedded in the surface of the platform, wherein each microfluidics structure comprises
   i) one or a plurality of fluid reservoirs,
   ii) one or a plurality of detection chambers,
   iii) one or a plurality of mixing microchannels and
   iv) one or a plurality of air ballast chambers
   wherein each of said fluid reservoir is fluidly connected to a mixing microchannel that is fluidly connected to a detection chamber and wherein the air ballast chamber is fluidly connected to the detection chamber by a microchannel, and wherein fluid within the microchannels of the platform is moved through said microchannels by centripetal force arising from rotational motion of the platform for a time and a rotational velocity sufficient to move the fluid through the microchannels.

2. A microsystem platform of claim 1 wherein each fluid reservoir further comprises a sample input port.

3. A microsystem platform of claim 1 wherein the detection reservoirs are optically transparent.

4. A microsystem platform of claim 1, wherein the air ballast chamber contains a volume of air sufficient to prevent fluid flow from the distal end of the mixing microchannel and into the detection chamber when the platform is rotated at a speed less than the maximum speed of platform rotation.

5. A microsystem platform of claim 1 wherein each fluid reservoir has a volumetric capacity of from about 1 nL to about 500 µL.

6. A microsystem platform of claim 1 wherein each detection reservoir has a volumetric capacity of from about 2 nL to about 1000 µL.

7. A microsystem platform of claim 1 wherein each mixing microchannel comprises a plurality of bends having angles greater than 90°.

8. A microsystem platform of claim 1 comprising from about 24 to about 10,000 microfluidics structures.

9. A microsystem platform of claim 1 wherein rotation of the platform motivates fluid through each of the microfluidics structures at a flow rate wherein the time the fluid is in the mixing microchannel is substantially the same in each of the microfluidics structures on the platform.

10. A microsystem platform of claim 9 wherein the flow rate of fluid through each of the mixing microchannels is from about 1 nL/s to about 100 µL/s.

11. A microsystem platform of claim 1 that is a circular disk having a radius of about 1 to about 25 cm.

12. The microsystem platform of claim 1, wherein the microsystem platform is constructed of a material selected from the group consisting of an organic material, an inorganic material, a crystalline material and an amorphous material.

13. The microsystem platform of claim 12, wherein the microsystem platform further comprises a material selected from the group consisting of silicon, silica, quartz, a ceramic, a metal or a plastic.

14. The microsystem platform of claim 1, wherein the microsystem platform has a thickness of about 0.1 to 100 mm, and wherein the cross-sectional dimension of the microchannels embedded therein is less than 1 mm and from 1 to 90 percent of said cross-sectional dimension of the platform.

15. The microsystem platform of claim 1, wherein the microsystem platform further comprises a multiplicity of air channels, exhaust air ports and air displacement channels.

16. A centripetally-motivated fluid micromanipulation apparatus that is a combination of
 a microsystem platform according to claim 1, and
 a micromanipulation device, comprising a base, a rotating means, a power supply and user interface and operations controlling means, wherein the rotating means is operatively linked to the microsystem platform and in rotational contact therewith
 wherein a volume of a fluid within the microchannels of the platform is moved through said microchannels by centripetal force arising from rotational motion of the platform for a time and a rotational velocity sufficient to move the fluid through the microchannels.

17. The apparatus of claim 16, wherein the rotating means of the device is a motor.

18. The apparatus of claim 16, wherein the device comprises a rotational motion controlling means for controlling the rotational acceleration and velocity of the microsystem platform.

19. An apparatus of claim 16 wherein the micromanipulation apparatus further comprises an optical detector that measures absorbance, fluorescence, epifluorescence or chemoluminescence.

20. An apparatus of claim 16 wherein the micromanipulation apparatus further comprises a scanning, imaging, or confocal microscopy detector.

21. An apparatus of claim 16 wherein the micromanipulation apparatus further comprises a radiometric detector.

22. The apparatus of claim 16, wherein the detector is an optical detector comprising a light source and a photodector.

23. A microsystems platform of claim 1, wherein the interior surface of the mixing microchannel has a contact angle greater than 90 degrees.

24. A method for homogenously mixing two or a plurality of different fluids, comprising the steps of:
 a) applying a volume of a first fluid to one or a plurality of fluid reservoirs of a microsystem platform of claim 1 when the platform is stationary;
 b) applying a volume of a second fluid to one or a plurality of fluid reservoirs of a microsystem platform of claim 1, wherein the fluid reservoir containging the first fluid is the same fluid reservoir containing the second fluid, or the fluid reservoirs containing the first and second fluids are fluidly connected to the same mixing microchannel;
 c) rotating the platform at an increasing rotational speed sufficient to motivate fluid flow from the fluid reservoir to the most distal extend of the mixing microchannel without motivating fluid flow into the detection chamber;
 d) rotating the platform at a decreasing rotational speed until all fluid in the mixing microchannel returns to the fluid reservoir
 e) repeating steps (c) and (d) for a number of repetitions sufficient to homogeneously mix the first and second fluids into a homogeneous mixture;
 f) rotating the platform at a rotational speed greater than the maximum speed of rotation in step (c) at a speed sufficient to motivate the homogeneously mixed fluid into the detection chamber; and
 g) detecting the homogenous mixture.

25. A microsystems platform of claim 1, wherein the interior surface of each of the microchannel comprises a graded surface to volume ratio, wherein the surface to volume ratio increases with distance from the axis of rotation.

26. A microsystems platform of claim 1, wherein the interior surface of each of the microchannels comprises a graded hydrophobic surface, wherein the hydrophobicity of the surface increases with distance from the axis of rotation.

27. A microsystem platfor of claim 1, wherein the interior surface of each of the microchannels comprises a graded surface to volume ratio, wherein the surface to volume ration increases with distance from the axis of rotation, and wherein the interior surface of each of the microchannels comprises a graded hydrophobic surface, wherein the hydrophobicity of the surface increases with distance from the axis of rotation.

* * * * *